United States Patent [19]

Partridge et al.

[11] Patent Number: 5,466,409
[45] Date of Patent: Nov. 14, 1995

[54] FORMING BELT FOR THREE-DIMENSIONAL FORMING APPLICATIONS

[75] Inventors: Mary E. Partridge, Appleton; Timothy J. Blenke, Neenah, both of Wis.; Stephen R. Everson, Danbury, Conn.; Carl G. Schroth, Kimberly; Michael B. Venturino, Appleton, both of Wis.

[73] Assignee: Kimberly-Clark Corporation, Neenah, Wis.

[21] Appl. No.: 139,461

[22] Filed: Oct. 19, 1993

[51] Int. Cl.⁶ .......................... B29C 43/02; B29C 43/06; B29C 43/08
[52] U.S. Cl. .................... 264/165; 264/112; 264/167; 264/518; 264/555; 425/81.1; 425/83.1
[58] Field of Search ................ 425/83.1, 80.1, 425/81.1; 264/165, 167, 112, 121, 518, 555

[56] References Cited

U.S. PATENT DOCUMENTS

| | | | |
|---|---|---|---|
| Re. 33,623 | 6/1991 | Anderson | 156/197 |
| 1,500,209 | 7/1924 | Shaw . | |
| 2,986,780 | 6/1961 | Bletzinger | 425/81.1 |
| 3,432,379 | 3/1969 | Anderson | 428/116 |
| 3,713,930 | 1/1973 | Levrini et al. | 156/147 |
| 3,741,840 | 6/1973 | Booth | 156/197 |
| 3,769,145 | 10/1973 | Gresham et al. | 156/197 |
| 3,973,291 | 8/1976 | Kolbach . | |
| 4,619,723 | 10/1986 | Takeagi | 425/80.1 |
| 4,626,184 | 12/1986 | Hammond | 425/83.1 |
| 4,632,862 | 12/1986 | Mullen | 428/116 |
| 4,666,647 | 5/1987 | Enloe et al. | 264/121 |
| 4,685,986 | 8/1987 | Anderson | 156/197 |
| 4,741,877 | 5/1988 | Mullane, Jr. | 264/504 |
| 4,761,258 | 8/1988 | Enloe | 264/518 |
| 4,877,474 | 10/1989 | Gross | 156/244.13 |
| 4,904,322 | 2/1990 | Mertens | 156/196 |
| 5,004,579 | 4/1991 | Wislinski et al. | 264/517 |
| 5,145,351 | 9/1992 | Rossi | 425/80.1 |

*Primary Examiner*—John Kim
*Attorney, Agent, or Firm*—Paul Yee

[57] ABSTRACT

A method and apparatus for forming a layer structure, such as an airlaid fibrous web, include a supplying mechanism for providing a stream of particulate material, such as fibers. Also included is a substantially endless, foraminous forming belt which has an appointed outward surface and a minimum thickness of at least about 3/16 inch. A selected contour is formed into the outward surface of the belt at selected locations, and the contour is distributed along a lengthwise machine-direction of the forming belt. The forming belt is configured to flex along a thickness direction thereof, and to recoverably bend and substantially straighten when traveling along a selected belt path circuit. A conveying mechanism moves the forming belt past the supplying mechanism along a forming path section of the belt circuit which is substantially straight, and moves the forming belt along a return path section of the belt circuit which includes curved portions therein. A vacuum mechanism draws a flow of air through the thickness of the forming belt to lay the particulate material onto the forming belt to form a layer structure, such as a web, having a top surface and a belt-side surface thereon. The web is thereby produced with a selected non-uniform thickness contour which is formed along the belt-side surface of the fibrous web. A driving mechanism moves the forming belt along the machine-direction at a selected speed, and a transporting mechanism removes the contoured web from the forming belt.

26 Claims, 6 Drawing Sheets

FORMING BELT FOR THREE-DIMENSIONAL FORMING APPLICATIONS

FIELD OF THE INVENTION

The present invention relates to a method and apparatus for to forming a layer structure with particulate materials, and providing the formed layer with a selected, contoured thickness dimension. More particularly, the invention relates to a method and apparatus for air laying fibers to form a fibrous web on an endless forming belt, and for selectively contouring the belt-facing side of the formed fibrous web.

BACKGROUND OF THE INVENTION

Devices for forming airlaid fibrous webs have been constructed to deposit fibrous material onto the foraminous surface of a moving forming belt having the configuration of an endless loop. For example, see U.S. Pat. No. 4,626,184 issued Dec. 2, 1986 to P. Hammond.

Devices for forming airlaid fibrous webs have also employed drumtype forming systems wherein the fibrous material is deposited onto a foraminous, outer peripheral surface of a revolving drum. For example, see U.S. Pat. No. 4,666,647 issued May 19, 1987, to K. Enloe et al. and entitled "Apparatus and Method for Forming a Laid Fibrous Web", and U.S. Pat. No. 4,761,258 issued Aug. 2, 1988, to K. Enloe and entitled "Controlled Formation of Light and Heavy Fluff Zones.

Conventional forming systems, such as those described above, have had various shortcomings. Forming drums have had relatively large diameters and can require excessive amounts of space. In addition, the forming drums have required complex sealing and baffling mechanisms to regulate the distribution of vacuum within the forming drum. Forming belt systems have had a limited ability to reliably produce desired contours in the thickness and basis weight of the formed fibrous web. The compactness of the forming belt system requires the forming belt to traverse around turn rolls having relatively small diameters. This requirement has limited the allowable thickness of the forming belt, and has limited the ability to incorporate a forming belt having significantly-sized depressions or other cavities formed into the belt surface. As a result, there has been a continued need for a belt-type of forming system that can more efficiently and more reliably produce a predetermined thickness and basis weight contour pattern onto the belt-side of the deposited, fibrous web.

BRIEF DESCRIPTION OF THE INVENTION

Generally stated, the present invention provides an apparatus for forming a layer structure from a particulate material. The apparatus includes a supplying means for providing the particulate material, and a substantially endless, foraminous forming belt. The forming belt has an appointed outward surface and a thickness which is greater than a desired contour to be formed on the layer structure. The forming belt includes a selected contour formed into the outward surface either continuously or at a plurality of selected locations distributed along a lengthwise, machine-direction of the forming belt. The forming belt is configured to flex along a thickness direction thereof, and to recoverably bend and substantially straighten when traveling along a selected belt path circuit. A conveying means moves the forming belt past the fiberizing means along a forming path section of said belt circuit which is substantially straight, and along a return path section of the belt circuit which includes curved portions therein. A vacuum means draws a flow of air through the thickness of the forming belt to lay the particulate material onto the forming belt to form a layer structure having a top surface and a belt-side surface thereof, thereby producing the layer structure with a selected non-uniform thickness contour which is formed along the belt-side surface of the fibrous web. A driving means moves the forming belt along the machine-direction at a selected speed, and a transporting means removes the contoured layer structure from the forming belt.

A further aspect of the invention provides a method for forming a layer structure, which includes the steps of supplying a particulate material, and providing a substantially endless foraminous forming belt having an appointed outward surface and a thickness which is greater than a desired contour to be formed on the layer structure. The forming belt has a selected contour formed into the outward surface either continuously along or at selected locations distributed along a lengthwise machine-direction of the forming belt. The forming belt is configured to flex along a thickness direction thereof and to recoverably bend and substantially straighten when traveling along a selected belt path circuit. The forming belt is conveyed past the step of supplying the particulate material and along a forming path section of the belt circuit which is substantially straight. The forming belt is also conveyed along a return path section of the belt circuit which includes curved portions therein. A flow of air is drawn through the thickness of the forming belt to lay the particulate material onto the forming belt to form a layer structure having a top surface and a belt-side surface thereof. The layer structure is thereby produced with a selected non-uniform thickness contour which is formed along the belt-side surface of the layer structure. The forming belt is driven along the machine-direction at a selected speed, and the contoured layer structure is transported from the forming belt.

The various aspects of the invention can advantageously form a fibrous web having a contoured thickness and basis weight while employing an endless belt type of forming system. The forming belt system can more effectively form predetermined contours in the thickness dimension and basis weight of the fibrous web without the need for complex and bulky drum-type forming systems.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

Figure 1:
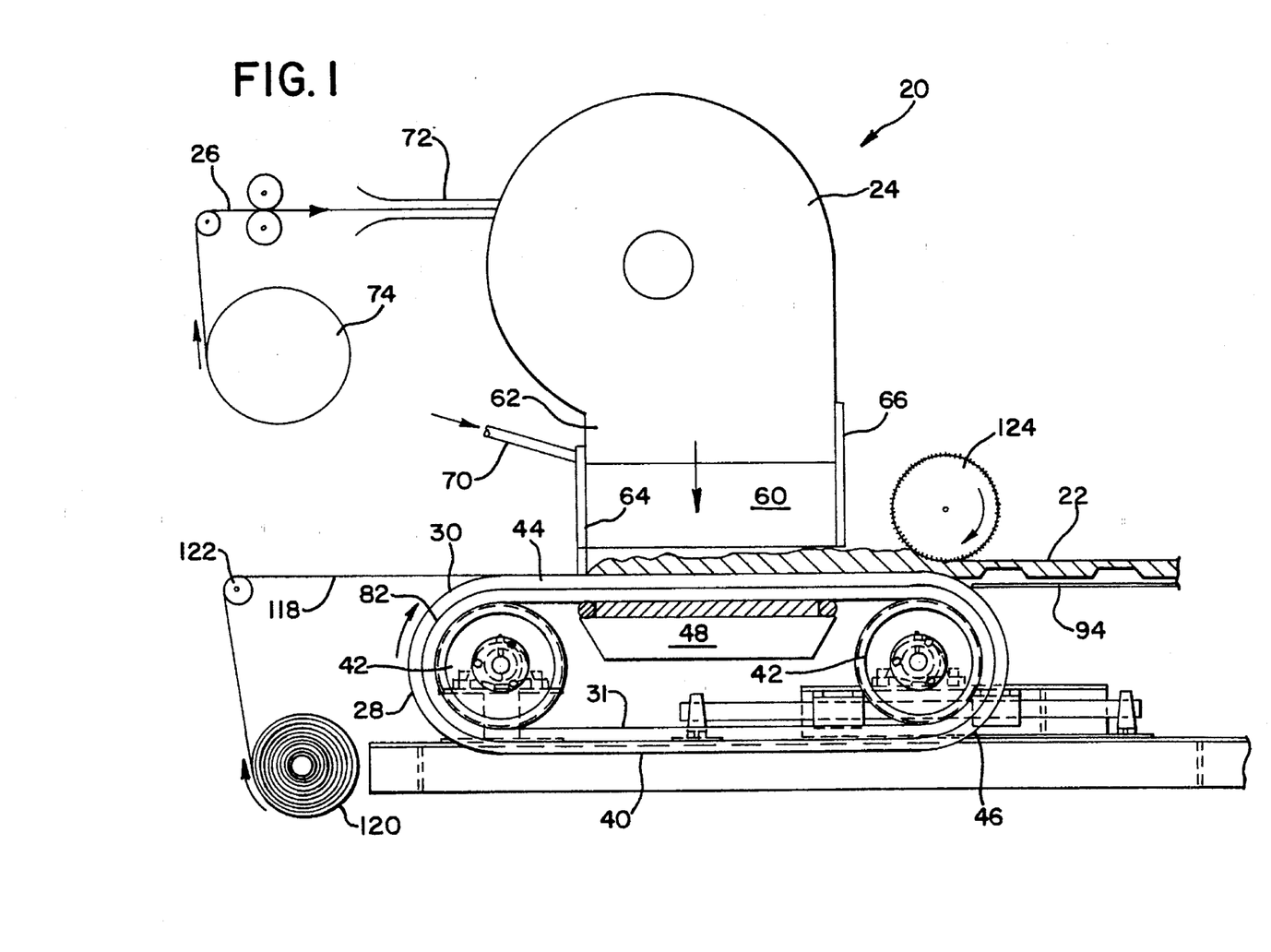
FIG. 1 representatively shows a side elevational view of an apparatus of the invention.
Figure 2:
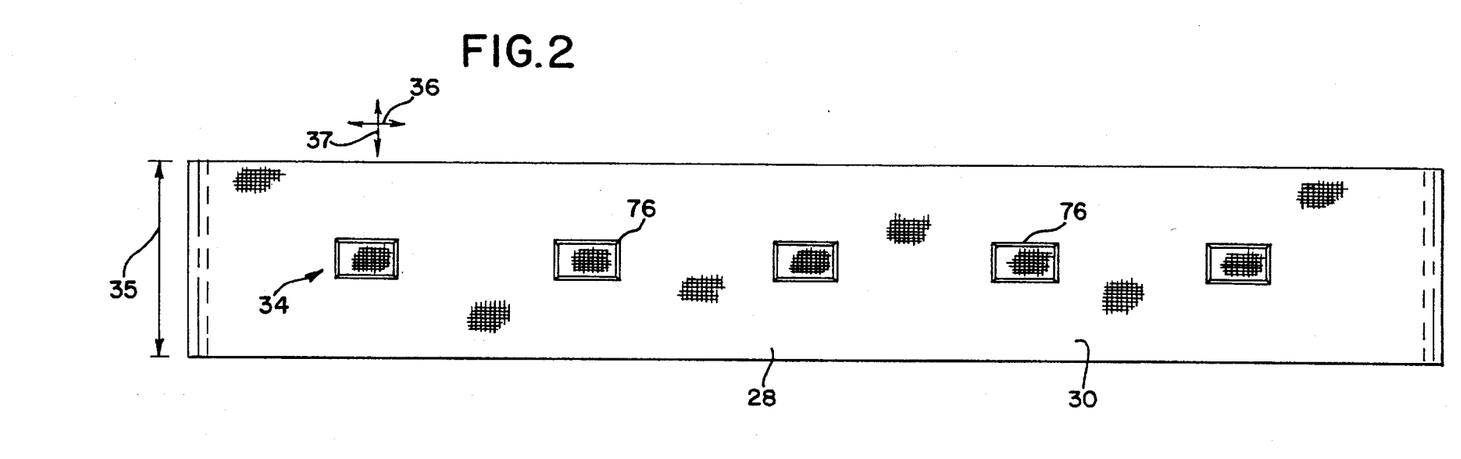
FIG. 2 representatively shows a top view of a forming belt system of the invention.
Figure 3:
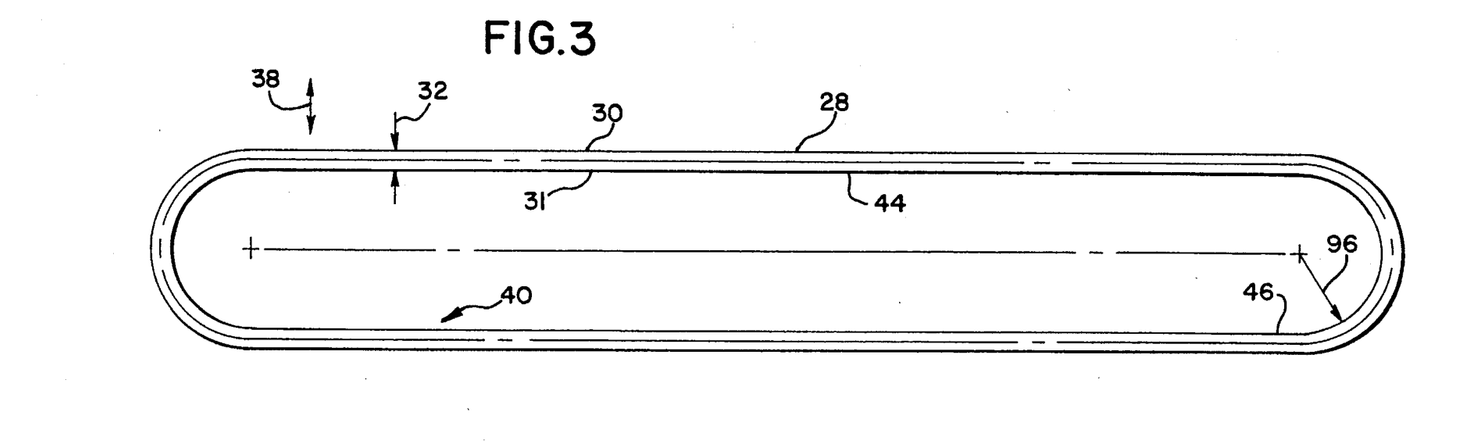
FIG. 3 representatively shows a side elevational view of a forming belt of the invention.
Figure 4:
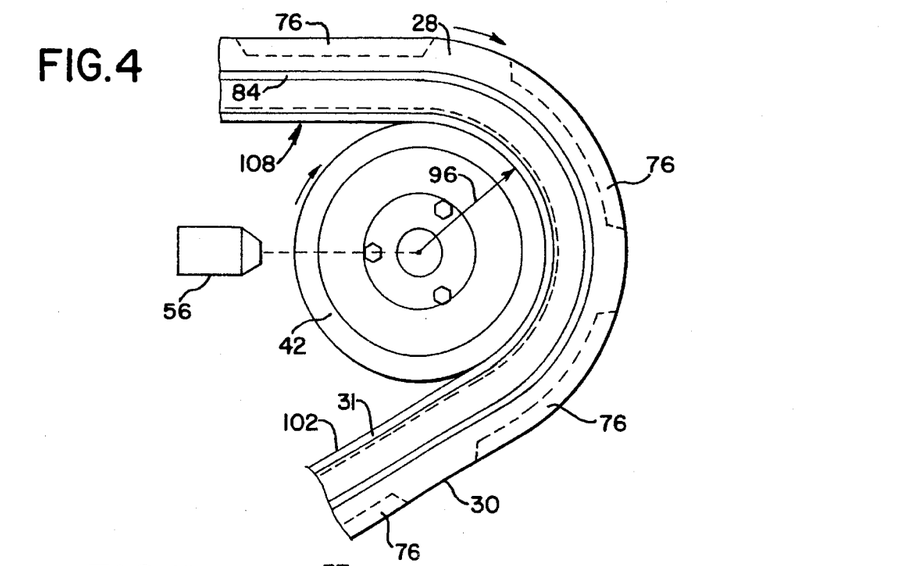
FIG. 4 representatively shows an enlarged side view of a forming belt system of the invention.
Figure 7C:
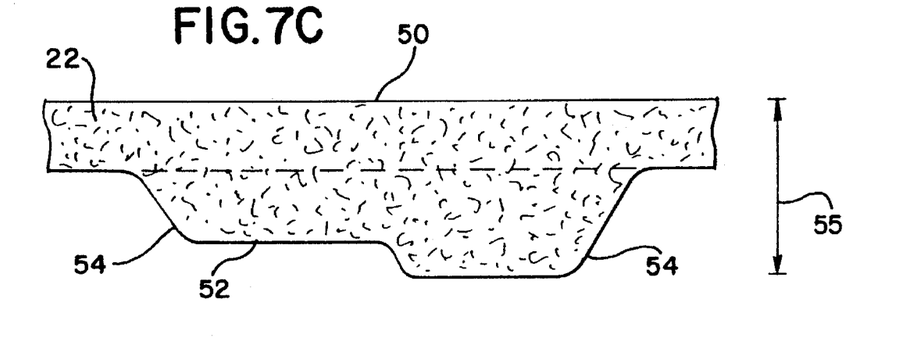
FIG. 7C representatively shows a cross-sectional side view of a web layer structure having the varied contour produced by the forming belt illustrated in FIGS. 7A and 7B.
Figure 8C:
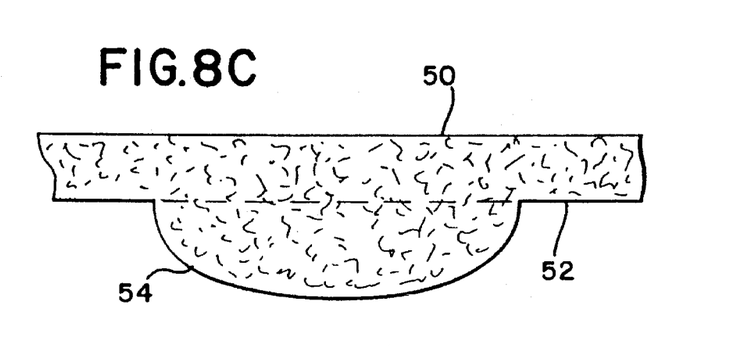
FIG. 8C representatively shows a cross-sectional side view of a web layer structure having the varied contour produced by the forming belt illustrated in FIGS. 8A and 8B.
Figure 9A:
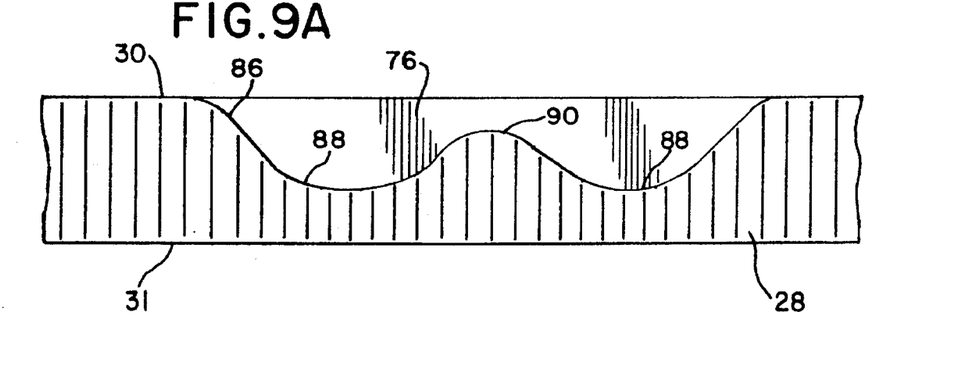
FIG. 9A representatively shows a cross-sectional side view of another individual cavity section which forms a portion of the valley-and-peak contour provided by another forming belt of the invention.
Figure 9B:
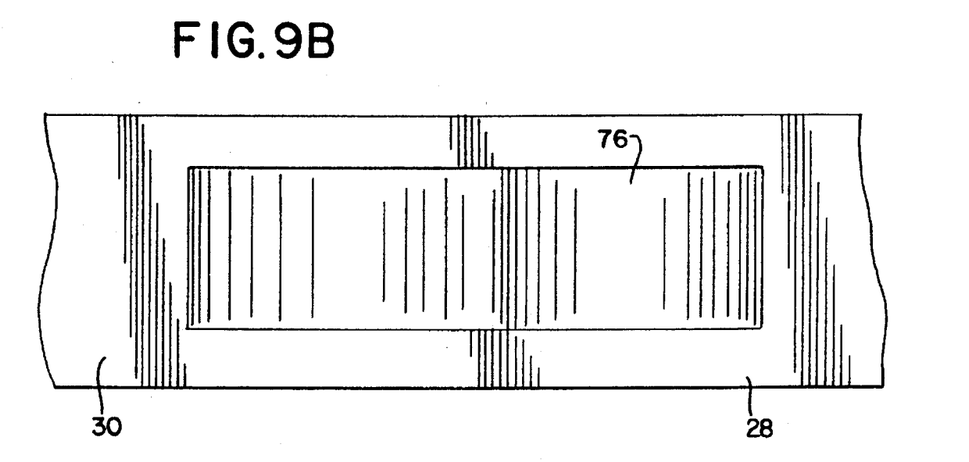
FIG. 9B representatively shows a top view of the cavity section illustrated in FIG. 9A.
Figure 9C:
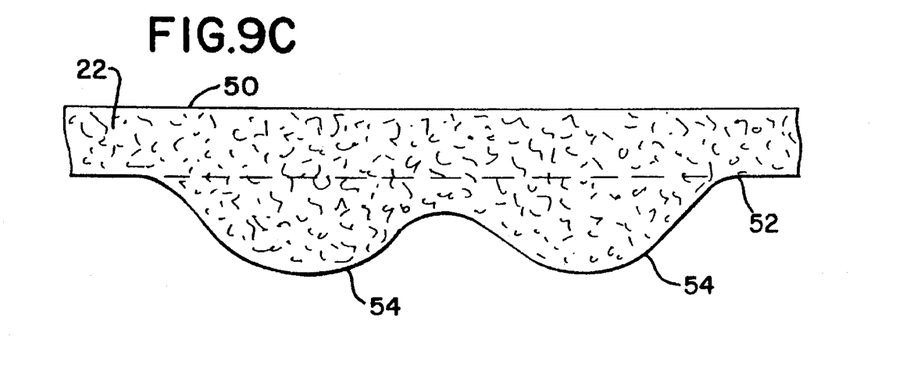
FIG. 9C representatively shows a cross-sectional side view of a web layer structure having the varied contour produced by the forming belt illustrated in FIGS. 9A and 9B.

With reference to FIG. 1, 2 and 3, an apparatus, generally shown at 20, can form a layer structure, such as fibrous web 22, and can be arranged to form a selected three-dimensional contour in the layer structure. The shown apparatus includes a supplying means, such as a fiberizing means comprising hammermill 24. The supplying means provides the particulate material, such as fibers 26, and can be configured to provide a stream of the material in selected quantities. A substantially endless, foraminous forming belt 28 has an appointed outward surface 30 cross extent 35 and has a minimum thickness dimension 32 which is at least about 3/16 in (about 0.48 cm). The forming belt includes a selected, three-dimensional contour 34 formed into outward surface 30 at selected locations distributed along a lengthwise machine-direction 36 of forming belt 28. In particular configurations of the invention, contour 34 is also distributed along the transverse, cross-direction 37 of the forming belt. Forming belt 28 is configured to flex along a thickness direction 38 of the belt. More particularly, the forming belt can recoverably bend around a selected turning radius 96 (FIG. 3) and substantially straighten when traveling along a selected belt path circuit 40. A conveying means, such as a system of conveying rollers 42, moves forming belt 28 past the supplying means along a forming path section 44 of belt circuit 40. The forming path section is substantially straight. In addition, the forming belt moves along a return path section 46 of the belt circuit, and the return path section includes curved portions therein. A vacuum means, such as a mechanism including vacuum box 48, draws a flow of air through the thickness 32 of forming belt 28 to lay fibrous material 26 onto the forming belt to form fibrous web 22. Accordingly, the present invention can provide an airlaid layer structure, such as the shown fibrous web, which has a top surface 50 and a belt-side surface 52 thereof (FIGS. 7C, 8C and 9C). The fibrous web can thereby be produced with a selected, non-uniform and three-dimensional thickness contour 54, which is formed along belt-side surface 52 of fibrous web 22. A driving means, such as drive motor 56 (FIG. 4), moves forming belt 28 along machine direction 36 at a selected speed. A transporting means, such as a suitable transport conveyor (not shown) and dead plate 94, removes the contoured fibrous web 22 from forming belt 28.

Particulate material 26 may generally have various potential forms and shapes, such as regular or irregular granules, flakes, rods, fibers, or the like or desired combinations thereof. In the illustrated embodiment, for example, the particulate material is primarily composed of fibers, and the fibers are airlaid to form a selected fibrous web. The fibers may be composed of natural fibers, synthetic fibers and blends thereof. Natural fibers include, for example, cotton linters and cellulosic fibers. In the illustrated embodiment, the fibrous material is composed of cellulosic wood pulp fibers commonly referred to as wood pulp "fluff". Fibrous webs produced by the present invention can be employed for various useful purposes. For example, the fibrous webs can be employed in the construction of absorbent bodies or pads for disposable absorbent articles, such as diapers, training pants, incontinence garments, feminine care products, wipes and the like.

The supplying means is suitably selected to operatively handle the chosen type of particulate material. For example, the supplying mechanism employed with the illustrated embodiment of the invention can include a hammermill 24 and a forming chamber 60. Suitable hammermills are, for example, available from JOA, a business having offices in Sheboygan Falls, Wisconsin, or Williams Pantent Crusher and Pulverizer Co., a business having offices at 2701 N. Broadway, St. Louis, Mo. Suitable forming chamber systems are, for example, available from Paper Converting Machine Company, a business having offices in Green Bay, Wisconsin. In a typical arrangement, a sheet of fibrous material is delivered from material supply 74 into inlet 72 of the hammermill. The hammermill includes a rotary hammer mechanism which strikes the sheet of fibrous material and disintegrates it into a plurality of individual discrete fibers. The fiberized material is directed into the top of forming chamber 60. The forming chamber includes two opposing side walls 62, an entrance wall 64 and an exit wall 66. In addition, baffles may be located inside forming chamber 60 to direct the fibrous materials toward selected locations of forming belt 28. In alternative configurations, another type of particulate material, such as particles of superabsorbent material may be introduced into forming chamber 60. For example, a supplemental supplying means, such as nozzle mechanism 70, may be employed to selectively direct the superabsorbent particles into a predetermined region of the forming chamber to form a selected distribution of superabsorbent within the layer structure provided by web 22. Examples of suitable superabsorbent distributions are described in U.S. Pat. No. 5,028,224 issued Jul. 2, 1991 to Pieper et al., the disclosure of which is hereby incorporated by reference to the extent that it is consistent herewith.

As representatively shown in FIGS. 1 and 3, forming belt 28 moves into forming chamber 60 through an appropriate opening which passes through entrance wall 64. The illustrated endless forming belt moves along a closed loop belt path circuit 40 which includes a substantially straight forming path section 44 and a generally curvilinear return path section 46. The shown curvilinear return path section includes an interconnected series of substantially straight portions and curved portions thereof. It should be readily apparent that alternative belt circuits may be composed of various other suitable combinations of straight and curved portions. With regard to the illustrated example, however, the forming belt is generally directed about closed path circuit 40 by a turning mechanism, such as provided by turn rollers 42.

As representatively shown in FIG. 2 and 3, forming belt 28 is in the form of a substantially endless, closed loop, and includes an appointed outward surface 30 and an appointed thickness dimension 32. The belt is sufficiently porous to the passage of air to provide a suitable foraminous substrate for receiving the deposit of airlaid fibrous material thereon. In particular aspects of the invention, the forming belt has an open area of at least about 20%. Preferably, the belt open area is at least about 45%, and more preferably, is at least about 75%. In other aspects of the invention, the belt open area is at least about 90%. By way of contrast, typical forming belts composed of perforated sheet material have exhibited an open area of about 20–50%, and forming belts composed of conventional hardware wire screens have exhibited an open area of about 10–50%.

The thickness 32 of forming belt 28 along its region of minimum thickness is at least about 3/16 in (about 0.48 cm). Preferably, the minimum thickness region of the forming belt has a thickness of at least about 3/8 in (about 0.95 cm), and more preferably has a thickness of at least about 1.5 in (about 3.8 cm) to provide desired benefits. The various illustrated embodiments of the invention, for example, can have the minimum thickness region located at the contoured regions formed into the thickness dimension of the forming belt.

In particular aspects of the invention, the region of greatest or maximum thickness of forming belt 28 can be distinctively configured with a thickness of up to about 12 in (about 30.5 cm). Alternatively, the greatest thickness region of the forming belt can have a thickness of up to about 3 in (about 7.6 cm), and optionally, can have a thickness of up to about 2 in (about 5.1 cm) to provide desired performance. In the illustrated embodiment, for example, the maximum thickness region of the belt is about 1.5 in (about 3.8 cm) thick.

In particular aspects of the invention, at least a longitudinally extending section of forming belt 28 has a region of greatest or maximum thickness which extends substantially continuously along substantially the entire length-wise dimension (machine-direction) of the forming belt. The belt region of maximum thickness can be located at one or more selected sections of the belt. In the illustrated embodiments, for example, the belt region of maximum thickness is provided by two, laterally-spaced, longitudinally-extending side sections 29 (FIG. 7B) of forming belt 28. It should be appreciated, however, that the belt region of maximum thickness need not have an absolutely constant thickness along the machine-direction of the forming belt.

Typical forming belt designs have been quite thin and flexible to accommodate travel around turn rollers of relatively small diameter. As a result, such forming belts have not been sufficiently thick and dimensionally stable to maintain the desired contoured configurations formed into the thickness dimension of the belt.

The present invention can advantageously provide a forming belt system which has adequate thickness to accommodate a desired depth contour. The profile of the depth contour is sufficient for forming desired thickness and basis weight profiles in a layer structure of selected particulate material. In addition, the forming belt system is sufficiently flexible to move about a relatively small turning radius while retaining an ability to recover its shape to substantially preserve the selected depth contour 54. As a result, the forming belt can improve the compactness and efficiency of the forming system.

In particular aspects of the invention, the ratio of the pocket or cavity depth 78 (FIG. 7A) to belt thickness 32 is not more than about 0.6. Alternatively, the ratio of cavity depth to belt thickness is not more than about 0.55, and optionally is not more than about 0.5 to provide desired benefits. In other aspects of the invention, the ratio of cavity depth to belt thickness is not less than about 0.1. Alternatively, the ratio of cavity depth to belt thickness is not less than about 0.15, and optionally is not less than about 0.2 to provide desired performance. For the purposes of determining this ratio, the cavity depth is the maximum depth of the cavity contour 80 provided into the forming belt, and the forming belt thickness is the thickness provided at its longitudinally-extending, belt region of maximum thickness.

In further aspects of the invention, the ratio of belt thickness 32 to turn radius 96 is not more than about 0.45 and alternatively is not more than about 0.4 to provide desired performance. In yet other aspects of the invention the ratio of belt thickness to turn radius is not less than about 0.003. Alternatively, the ratio of belt thickness to turn radius is not less than about 0.05, and optionally is not less than about 0.10 to provide desired benefits. For the purposes of determining this ratio, the forming belt thickness is the thickness provided at its longitudinally-extending, belt region of maximum thickness.

The forming belt includes a selected three-dimensional contour 34 formed into its outward surface 30 at selected locations along the machine direction 36 and/or cross direction 37 of the forming belt. The three-dimensional contour is additional to and substantially greater than the ordinary surface texture, wire-weave, porosity or other general unevenness provided by the forming belt material itself. The contour is molded, machined or otherwise formed into the depth or thickness of the material of the forming belt to form predetermined void spaces having the sides and bottom regions thereof bounded by the material of the forming belt. The regions of the belt inside surface 31 which are located opposite to the void spaces are substantially free of corresponding projections or deformations.

For example, contour 34 may comprise at least one, generally continuous channel which extends along the machine direction of the forming belt. In particular aspects of the invention, the cross-directional width of the channel may be substantially uniform or may be non-uniform. Other aspects of the invention can incorporate a channel having a varied, contoured depth which changes along the length dimension of the channel. In additional aspects of the invention, a selected contour pattern composed of a plurality of similar or different channels may be formed into the outward surface of the forming belt.

In further aspects of the invention, contour 34 may include a plurality of individual, discrete cavities 76 distributed and intermittently positioned along the machine direction 36 of forming belt 28. The cavities may be regularly spaced or, optionally, irregularly spaced along the machine direction of the forming belt.

The shape of the cavity along the outward surface 30 of forming belt 28 can be of any selected configuration. For example, the shape of the cavity may be circular. In the illustrated embodiment representatively shown in FIG. 2, the cavity has a generally rectangular shape.

Figure 7A:
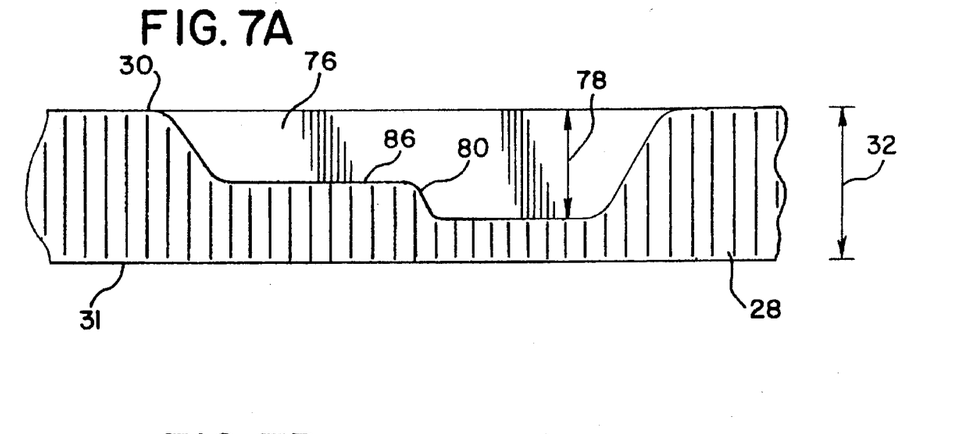
FIG. 7A representatively shows a cross-sectional side view of an individual cavity section which forms a portion of the stepped contour provided by a forming belt of the invention.

Each cavity 76 can include a predetermined cavity depth 78 (FIG. 7A). The cavity depth may be substantially uniform or may have a selected depth contour pattern 80. Forming belt 28 can be distinctively configured to accommodate a maximum cavity depth of up to about 5.75 in (about 14.6 cm). In addition, the accommodated cavity depth can be at least about 0.003 in (about 0.016 cm), and preferably, is at least about 0.375 in (about 0.95 cm) to provide desired performance.

Figure 7B:
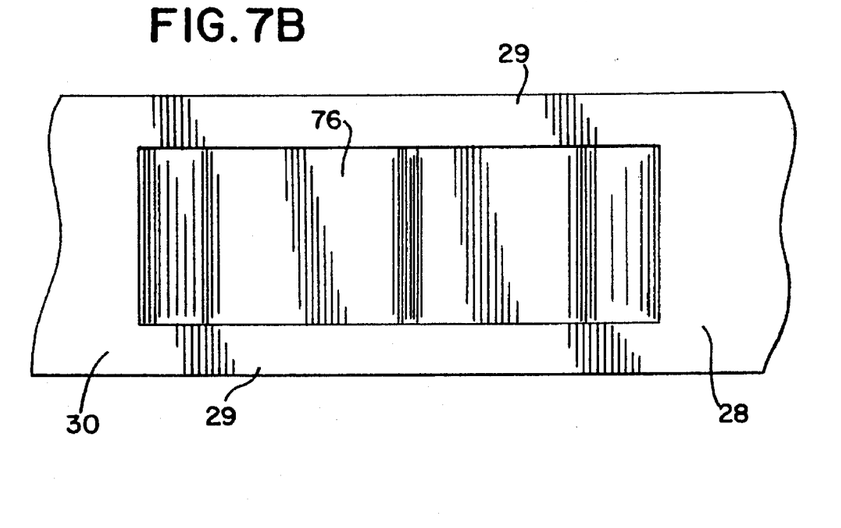
FIG. 7B representatively shows a top view of the cavity section illustrated in FIG. 7A.

With reference to the example representatively shown in FIGS. 7A and 7B, cavity 76 has a contoured depth profile in the general form of two steps 86 positioned at different depths into forming belt 28. Optionally, the depth contour could include a plurality of more than two discrete steps or plateau regions.

Figure 8A:
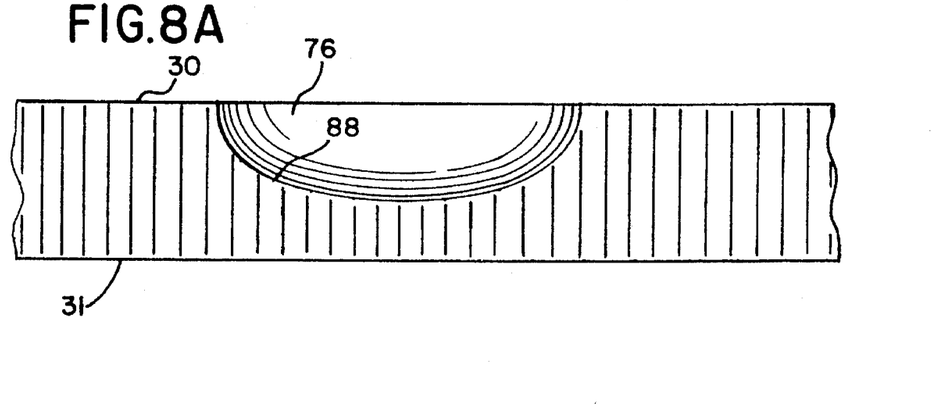
FIG. 8A representatively shows a cross-sectional side view of another individual cavity section which forms a portion of the arcuate contour provided by another forming belt of the invention.
Figure 8B:
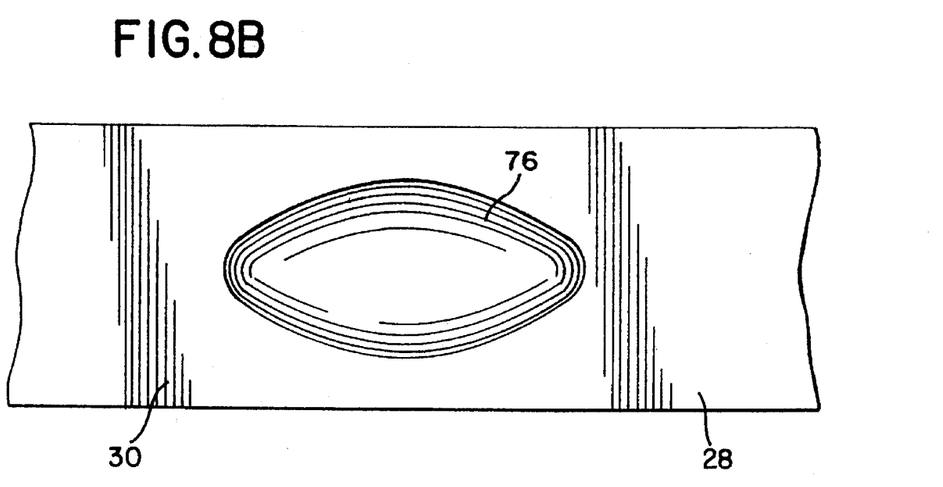
FIG. 8B representatively shows a top view of the cavity section illustrated in FIG. 8A.

FIGS. 8A and 8B representatively show another cavity 76 having a curvilinear depth profile with a single valley region 88. FIGS. 9A and 9B illustrate an example of cavity 76 having a corrugated profile wherein the depth contour includes two or more discrete valley regions 88 along with one or more interposed peak regions 90.

The present invention can optionally include a combination of the various discrete cavities and channels formed into outward surface 30 in a selected pattern. The channels and cavities may be interconnected and/or noncontiguously spaced-apart to produce desired patterns and three-dimensional contours.

Forming belt 28 is constructed and configured to flex along a thickness direction 38 thereof. As the forming belt travels around belt circuit 40, the forming belt is capable of recoverably bending along the curved portions of the belt circuit, and is capable of substantially restraightening when traveling along straight portions of the belt path circuit. In particular, forming belt 28 is constructed such that it can bend to follow a selected turning radius 96 (FIG. 4) defined by a curved portion of the belt path circuit, and then unbend to return to a substantially straight configuration to travel along straight portions of the belt path circuit.

In the illustrated embodiment, for example, the forming belt can recoverably bend and then substantially straighten when traveling at a speed of about 50 ft/min (about 25.4 cm/sec) around a turning radius of 3.6 in (9.2 cm) while at the same time moving through an arc length of at least about 90 degrees. The forming belt can also recoverably bend and substantially straighten when traveling at a speed of about 50 ft/min through an arc length of about 90 degrees around a turning radius of 7.2 in. Preferably, the forming belt can travel about the turning radius while moving through an arc length of 135 degrees, and more preferably can travel about the turning radius while moving through an arc length of 180 degrees to provide desired benefits.

As each incremental segment of forming belt 28 traverses along the entire belt path circuit, the belt contour 34 formed into the outward surface 30 of forming belt 28 may become deformed as it traverses through the curved portions of the path circuit. More particularly, the outlines of the individual portions of the belt contour may deform in the machine-direction and cross-direction of the belt. In a particular aspect of the invention, the thickness dimension of the belt contour remains substantially undeformed when moving through the curved portions of the path circuit. When the forming belt moves through a substantially straight portion of the belt path circuit, such as forming path section 44, the belt contour 34 is substantially reestablished. As a result, as each section of the forming belt is reconveyed along forming path section 44, it is capable of recovering the shape intended for reproducing the desired fibrous web contour 54 into the belt side surface 52 of fibrous web 22.

To provide the desired capability of bending and restraightening through a multiplicity of sequential operations, forming belt 28 is formed of a flexible and durable belt material. For example, the forming belt may be constructed from a synthetic polymer type of material, such as polyurethane. Alternatively, forming belt 28 may be constructed from an articulated, honeycomb material, such as a trapezoidal honeycomb material. Another example of a suitable material is an I-beam honeycomb material constructed from a durable material, such as stainless steel, and available from Eldim Inc., a business having offices in Woburn, Mass.

In a particular aspect of the invention, forming belt 28 includes a restraining means 82 for maintaining a selected machine-direction length dimension of the forming belt. The restraining mechanism may, for example, comprise a chain, cable, flexible sheet or other articulatable mechanism that is sufficiently resistent to stretching or elongation. In the embodiment illustrated in FIG. 4, for example, the restraining mechanism comprises a stranded cable 84 composed of stainless steel. The cable can have a diameter of about 0.062 in (about 0.16 cm) and can be configured to exhibit an elongation of not more than about 0.00138 in/in when subjected to an applied tensile force of 325 lbs-force (about 1446N).

The restraining means is operably connected to forming belt 28 with suitable fastening means, such as retaining pins, crimping, fusing, welding or the like. In the representatively shown embodiment, for example, a cable 84 is attached by intermittent crimping to each of the two opposed, lateral side surfaces of forming belt 28. Alternatively, each cable 84 may be attached by intermittent welding to the two side surfaces of forming belt 28. The welds can be provided at discrete .Spaced-apart locations along the length of each cable to help preserve the flexibility of the cable.

Typically, the restraining means is attached to forming belt 28 at a location which approximately coincides with the cross-directionally aligned, bending axis about which the forming belt is intended or expected to flex when it deforms to curve around the non-linear sections of belt path 40. In particular aspects of the invention, for example, the restraining means can be selectively positioned along the thickness dimension of the belt at a location which approximately coincides with the "neutral" axis of the forming belt. Since the bending of forming belt 28 produces zero bending stress along the neutral axis, the forces and loads counteracted by the restraining means will be substantially limited to generally constant loads directed along the length of the forming belt.

In another aspect of the invention, forming belt 28 can include a timing means for maintaining a desired registration of the forming belt movement relative to the movement of other portions of the web forming apparatus 20. For example, the timing mechanism may be configured to maintain a desired registration between the forming belt movement relative to a movement of transport conveyor 58. Suitable timing mechanisms are, for example, described in U.S. Pat. No. 5,235,515; entitled METHOD AND APPARATUS FOR CONTROLLING THE CUTTING AND PLACEMENT OF COMPONENTS ON A MOVING SUBSTRATE, AND ARTICLE MADE THEREWITH; issued Aug. 10, 1993 to Ungpiyakul et al.; the disclosure of which is hereby incorporated by reference to the extent that it is consistent herewith.

In a further aspect of the invention, the method and apparatus can include a tracking means for providing a selected cross-directional positioning of forming belt 28 as it moves along belt path circuit 40. In the illustrated embodiment, for example, tracking mechanism can be provided by a timing belt device or a pulley/belt type of mechanism. Suitable devices are available from Woods Company, a business having offices located at Chambersburg, Pennsylvania.

Figure 6:
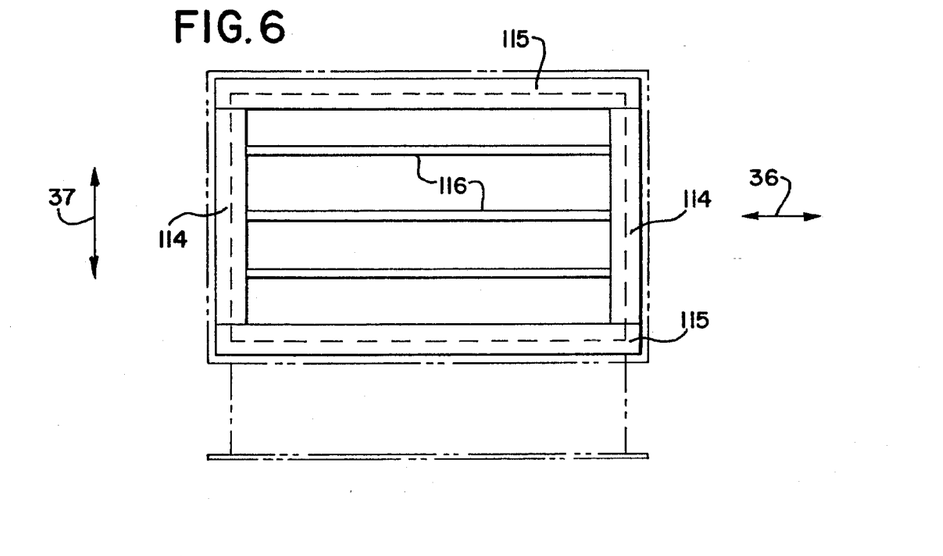
FIG. 6 representatively shows a top view of the vacuum box region of the forming belt system of the invention.

The invention can further include a thickness-controlling means for maintaining a selected thickness dimension 32 of forming belt 28 and for reducing wear and erosion of the forming belt. For example, the thickness controlling mechanism 108 can include a plurality of stationary wear bars 114 mounted onto vacuum box 48 and aligned generally along the cross-direction 37 of the forming belt (FIG. 6). Optionally, the thickness controlling mechanism 108 can include a plurality of wear bars connected to forming belt 28 and aligned generally along the cross-direction 37 of the forming belt.

Figure 5:
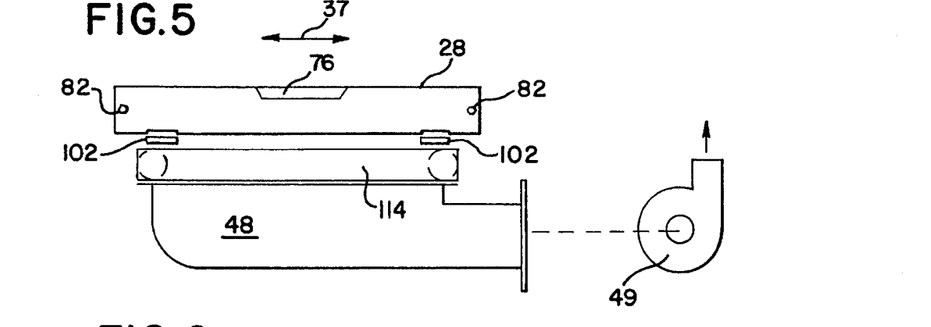
FIG. 5 representatively shows a end view of the vacuum box region of the forming belt system of the invention.

The vacuum mechanism for drawing a flow of air through the thickness of forming belt 28 typically includes a vacuum box 48 and a vacuum fan 49 (FIG. 5). Vacuum box 48 is positioned within or adjacent to forming chamber 60 and located immediately below the forming path section 44 of forming belt 28. Vacuum fan 49 is suitably sized to draw sufficient amounts of air to operably form the desired layer structure on the outward surface 30 of forming belt 28. In the illustrated embodiment, for example, vacuum fan 49 has a flow capacity of at least about 100 cfm (cubic feet per minute) to operably produce fibrous web 22.

To help support forming belt 28 and to reduce wear and erosion of the area over and adjacent vacuum box 48, the various aspects of the invention can incorporate a system of cross-direction wear bars 114 and machine-direction wear bars 115, as representatively shown in FIGS. 5 and 6. In alternative configurations, the region proximate to vacuum box 48 can be configured with a multiplicity of supplemental, machine-direction wear bars 116 that extend substantially parallel to the movement direction of forming belt 28. The illustrated arrangement shown in FIG. 6, for example, includes more than two side-by-side wear bars.

With reference to the representative arrangement illustrated in FIG. 7C, the formed layer structure of the selected particulate material has a top surface 50 and a belt-side surface 52. The illustrated fibrous web 22, for example, can thereby be provided with a selected, non-uniform and three-dimensional thickness contour 54 which is produced along the belt-side surface of the web. In addition, the web can have a non-uniform basis weight pattern or profile which is formed and distributed in general correspondence with the associated, profiled thickness contour 54. In particular aspects of the invention, the relatively thin sections of contour 54 have a web thickness dimension 55 which is not more than about 50% of the thickness of the relative thick sections of the web contour 54. The relatively thin sections of contour 54 have a web thickness dimension 55 which is alternatively not more than about 40%, and optionally not more than about 30%, of the thickness of the relative thick sections of web contour 54 to provide desired levels of effectiveness.

In further aspects of the invention, the relatively thin sections of contour 54 can have a local web basis weight which is less than the basis weight of the relatively thicker sections of the contour. In particular the relatively thin sections of contour 54 can have a local web basis weight which is not more than about 70% of the basis weight of the relatively thicker sections of the web contour 54. Alternatively, the relatively thinner sections of contour 54 have a local web basis weight which is not more than about 60%, and optionally is not more than about 50% of the basis weight of the relatively thicker sections of web contour 54 to provide desired performance benefits.

A suitable driving mechanism, such as drive motor 56 (FIG. 4), is constructed and arranged to move forming belt 28 through forming chamber 60 along machine direction 36 at a speed of at least about 50 feet per minute (about 0.25 m/sec). Alternatively, the driving mechanism moves forming belt at a speed of at least about 100 feet per minute (about 0.5 meters per second). In particular arrangements of the invention, the driving mechanism is configured to move forming belt 28 at a maximum speed of not more than about 1300 feet per minute (about 6.6 meters per second). Alternatively, the driving mechanism moves forming belt 28 at a speed of not more than about 900 feet per minute (about 4.6 meters per second).

The driving mechanism operably engages forming belt 28 to produce the desired motion. The engagement can be accomplished by any suitable means. In the illustrated embodiment, for example, engagement mechanism comprises a friction drive employing timing belts 102. More particularly, a timing belt is operably connected to forming belt 28 at laterally opposed side regions of the forming belt. The timing belts are suitably located and connected to accommodate the desired flexure and recovery of the forming belt. In alternative configurations, the engagement mechanism can comprise an intermeshing type of drive, such as a system of chain and sprocket mechanisms.

A transporting mechanism, such as a conveyor, provides for a removal of the contoured fibrous web 22 from forming belt 28 and carries the web to other manufacturing stations for further processing. In the illustrated embodiment, for example the transporting mechanism is provided by a dead plate 94 and a pair of nipping conveyer rollers which draw the web over and across the dead plate.

With reference again to FIG. 1, the invention can further include a wrapping mechanism for placing a layer of wrapsheet material 118 adjacent either or both of the major facing surfaces of fibrous web 22. In the illustrated embodiment, for example, wrapsheet material 118 is delivered from wrapsheet supply 120 along guide rollers 122 to a position which is superjacent the outward surface 30 of the forming path section 44 of forming belt 28. The particulate layer of fibrous web 22 is then formed on top of the layer of wrapsheet 118. Wrapsheet 118 can have a cross-directional width which is greater than the width of fibrous web 22. As a result, the lateral side edges of the wrapsheet 118 can be folded over the side edges of fibrous web 22 to thereby substantially envelop the fibrous web with wrapsheet material 118. The folding of wrapsheet 118 can be accomplished by conventional mechanisms, such as folding boards.

The invention can also include a scarfing mechanism, such as scarfing roll 124, which is configured to shape top surface 50 of fibrous web 22. For example, scarfing roll 124 can be configured to substantially level top surface 50 by abrading selected quantities of fibrous material 26 away from top surface 50. The abraded and separated fibrous material can be removed away from fibrous web 22 in a conventional manner, such as by an air flow directed out from a suitable exhaust duct (not shown).

Having thus described the invention in rather full detail, it will be readily apparent to a person having ordinary skill in the art, that various changes and modifications can be made without departing from the spirit of the invention. All of such changes and modifications are contemplated as being within the scope of the present invention, as defined by the subjoined claims.

We claim:

1. An apparatus for forming a layer structure, comprising:
   supplying means for providing a particulate material;
   a substantially endless, foraminous forming belt which has an appointed outward surface and a minimum thickness of at least about 3/16 inch, said forming belt constructed of a honeycomb material providing an open area of at least about 75%, said forming belt including a selected contour formed into said outward surface at selected locations distributed along a length-wise machine-direction of said forming belt honeycomb material, said forming belt configured to flex along a thickness direction thereof and to recoverably bend and substantially straighten when traveling along a selected belt path circuit and said forming belt having a thickness dimension which remains substantially undeformed when moving through curved portions of said belt path;
   restraining means for maintaining a selected length dimension of said forming belt, said restraining means connected to said forming belt at a location along a thickness dimension thereof, said location approximately coinciding with a bending neutral axis of said forming belt;
   conveying means for moving said forming belt past said supplying means along a forming path section of said belt circuit which is substantially straight, and along a return path section of said belt circuit which includes curved portions therein;
   vacuum means for drawing a flow of air through said thickness of said forming belt to lay said particulate material onto said forming belt to form a particulate layer having a top surface and a belt-side surface thereof, thereby producing a contoured layer having a selected nonuniform thickness contour which is formed along said belt-side surface of said contoured layer;
   driving means for moving said forming belt along said machine-direction at a selected speed; and
   transporting means for removing said contoured layer from said forming belt.

2. An apparatus as recited in claim 1, wherein said selected contour is formed into said outward surface at a plurality of discrete intermittent locations distributed along said machine-direction of said forming belt.

3. An apparatus as recited in claim 1, wherein said selected belt contour, after traversing said belt path circuit, is substantially reestablished along sections of said forming belt which are being reconveyed along said forming path section of said belt circuit.

4. An apparatus as recited in claim 1, wherein said selected belt contour includes a selected pattern of channels.

5. An apparatus as recited in claim 1, wherein said selected belt contour includes a selected pattern of discrete cavities.

6. An apparatus as recited in claim 1, wherein said selected belt contour includes a pattern composed of a combination of channels and discrete cavities.

7. An apparatus as recited in claim 1, wherein said forming belt honeycomb material is configured to recoverably bend and substantially straighten when traveling at a speed of about 50 ft/min through an arc length of about 90 degrees around a turning radius of 3.6 in.

8. An apparatus as recited in claim 1, wherein said forming belt comprises an articulated, I-beam honeycomb material.

9. An apparatus as recited in claim 1, wherein said forming belt contour includes at least one cavity formed into said outward surface to a depth of at least about 3/8 in.

10. An apparatus as recited in claim 1, wherein said honeycomb material of said forming belt is configured to recoverably bend and substantially straighten when traveling at a speed of about 50 ft/min through an arc length of about 90 degrees around a turning radius of 7.2 in.

11. An apparatus as recited in claim 1, wherein said selected contour formed into said forming belt provides a cavity depth, and wherein a ratio of said cavity depth to said thickness dimension of said forming belt is not more than about 0.6.

12. An apparatus as recited in claim 11, wherein said selected contour formed into said forming belt provides a cavity depth, and wherein a ratio of said cavity depth to said thickness dimension of said forming belt is not more than about 0.55.

13. An apparatus as recited in claim 12, wherein said selected contour formed into said forming belt provides a cavity depth, and wherein a ratio of said cavity depth to said thickness dimension of said forming belt is not more than about 0.5.

14. A method for forming a layer structure comprising the steps of:
   (a) supplying a particulate material;
   (b) providing a substantially endless foraminous forming belt constructed of a honeycomb material which provides an open area of at least about 75%, said forming belt having an appointed outward surface, a minimum thickness of at least about 3/16 in, and having a selected contour formed into said outward surface at selected locations distributed along a length-wise machine-direction of said forming belt honeycomb material;
   (c) configuring said forming belt to flex along a thickness direction thereof and to recoverably bend and substantially straighten when traveling along a selected belt path circuit, wherein said forming belt has a thickness dimension which remains substantially underformed when moving through curved portions of said belt path;
   (d) conveying said forming belt past said supplying step (a) along a forming path section of said belt circuit which is substantially straight, and along a return path section of said belt circuit which includes curved portions therein;
   (e) drawing a flow of air through said thickness of said forming belt to lay said particulate material onto said forming belt to form a particulate layer structure having a top surface and belt-side surface thereof, thereby producing a contoured layer structure with a selected nonuniform thickness contour which is formed along said belt-side surface of said contoured layer structure;
   (f) driving said forming belt along said machine-direction at a selected speed;
   (g) restraining said forming belt at a location along a thickness location thereof to maintain a selected length dimension of said forming belt, said location approximately coinciding with a bending neutral axis of said forming belt; and
   (h) transporting said contoured layer structure from said forming belt.

15. A method as recited in claim 11, further comprising the step of forming said selected contour into said outward surface at a plurality of discrete intermittent locations distributed along said machine-direction of said forming belt.

16. A method as recited in claim 14, further comprising the step of providing said selected belt contour with a selected pattern of channels.

17. A method as recited in claim 14, further comprising the step of providing said selected belt contour with a selected pattern of discrete cavities.

18. A method as recited in claim 17, further comprising the step of providing said forming belt contour with at least one cavity formed into said outer surface to a maximum depth of at least about 3/8 inch.

19. A method as recited in claim 14, further comprising the step of providing said selected contour with a pattern composed of a combination of channels and discrete cavities.

20. A method as recited in claim 14, further comprising the step of configuring said forming belt to recoverably bend and substantially straighten when traveling at a speed of about 50 ft/min through an arc length of about 90 degrees around a turning radius of 3.6 in.

21. A method as recited in claim 20, wherein said driving step is arranged to move said forming belt at a speed of at least about 100 ft/min.

22. A method as recited in claim 14, further comprising the step of providing said forming belt in an arrangement composed of an I-beam honeycomb material.

23. A method as recited in claim 14, further comprising the step of configuring said forming belt to recoverably bend and substantially straighten when traveling at a speed of about 50 ft/min through an arc length of about 90 degrees around a turning radius of 7.2 in.

24. A method as recited in claim 14, wherein said providing step (b) includes the step of forming said selected contour to include a cavity depth, and wherein a ratio of said cavity depth to said thickness dimension of said forming belt is not more than about 0.6.

25. A method as recited in claim 24, wherein said providing step (b) includes the step of forming said selected contour to include a cavity depth, and wherein a ratio of said cavity depth to said thickness dimension of said forming belt is not more than about 0.55.

26. A method as recited in claim 25, wherein said providing step (b) includes the step of forming said selected contour to include a cavity depth, and wherein a ratio of said cavity depth to said thickness dimension of said forming belt is not more than about 0.5.

* * * * *